(12) United States Patent
Brighton (10) Patent No.: US 8,313,908 B2
(45) Date of Patent: *Nov. 20, 2012

(54) REGULATION OF STEM CELL GENE PRODUCTION WITH SPECIFIC AND SELECTIVE ELECTRIC AND ELECTROMAGNETIC FIELDS

(75) Inventor: Carl T. Brighton, Malvern, PA (US)

(73) Assignee: The Trustees Of The University Of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/303,497

(22) Filed: Nov. 23, 2011

(65) Prior Publication Data

US 2012/0149968 A1    Jun. 14, 2012

Related U.S. Application Data

(63) Continuation-in-part of application No. 13/242,606, filed on Sep. 23, 2011, which is a continuation of application No. 12/167,283, filed on Jul. 3, 2008, now Pat. No. 8,065,015, which is a continuation of application No. 10/257,126, filed as application No. PCT/US01/05991 on Feb. 23, 2001, now Pat. No. 7,465,566.

(60) Provisional application No. 60/184,491, filed on Feb. 23, 2000.

(51) Int. Cl.
C12Q 1/68 (2006.01)
C12N 13/00 (2006.01)

(52) U.S. Cl. .................. 435/6.1; 435/173.8; 607/50

(58) Field of Classification Search .................. None
See application file for complete search history.

(56) References Cited

U.S. PATENT DOCUMENTS

| | | | |
|---|---|---|---|
| 4,430,999 A | 2/1984 | Brighton et al. | |
| 4,442,846 A | 4/1984 | Brighton et al. | |
| 4,467,808 A | 8/1984 | Brighton et al. | |
| 4,467,809 A | 8/1984 | Brighton et al. | |
| 4,487,834 A | 12/1984 | Brighton | |
| 4,506,674 A | 3/1985 | Brighton et al. | |
| 4,509,520 A | 4/1985 | Dugot | |
| 4,535,775 A | 8/1985 | Brighton et al. | |
| 4,549,547 A | 10/1985 | Brighton et al. | |
| 4,600,010 A * | 7/1986 | Dugot | 607/27 |
| 4,683,873 A | 8/1987 | Cadossi et al. | |
| 4,998,532 A | 3/1991 | Griffith | |
| 5,014,699 A | 5/1991 | Pollack | |
| 5,038,797 A | 8/1991 | Batters | |
| 5,269,746 A | 12/1993 | Jacobson | |
| 5,273,033 A | 12/1993 | Hoffman | |
| 5,338,286 A | 8/1994 | Abbott et al. | |
| 5,374,283 A | 12/1994 | Flick | |
| 5,743,844 A | 4/1998 | Tepper et al. | |
| 5,968,527 A | 10/1999 | Litovitz | |
| 6,083,149 A | 7/2000 | Wascher et al. | |
| 6,132,362 A | 10/2000 | Tepper | |
| 6,186,940 B1 | 2/2001 | Kirschbaum | |
| 6,261,221 B1 | 7/2001 | Tepper et al. | |
| 6,292,699 B1 | 9/2001 | Simon et al. | |
| 6,485,963 B1 | 11/2002 | Wolf et al. | |
| 6,605,089 B1 | 8/2003 | Michelson | |
| 6,747,004 B1 | 6/2004 | Tabibzadeh | |
| 6,919,205 B2 | 7/2005 | Brighton | |
| 6,955,642 B1 | 10/2005 | Simon | |
| 7,022,506 B2 | 4/2006 | Brighton et al. | |
| 7,130,692 B2 | 10/2006 | Brighton et al. | |
| 7,158,835 B2 | 1/2007 | Brighton et al. | |
| 7,167,753 B2 | 1/2007 | Brighton et al. | |
| 7,215,995 B2 | 5/2007 | Brighton et al. | |
| 7,374,916 B2 | 5/2008 | Brighton | |
| 7,429,471 B2 | 9/2008 | Brighton | |
| 7,465,546 B2 | 12/2008 | Brighton | |
| 7,465,566 B2 | 12/2008 | Brighton et al. | |
| 8,065,015 B2 | 11/2011 | Brighton et al. | |
| 2002/0009797 A1 | 1/2002 | Wolf et al. | |
| 2002/0038137 A1 | 3/2002 | Stein | |

(Continued)

FOREIGN PATENT DOCUMENTS

| | | |
|---|---|---|
| EP | 0652028 | 5/1995 |
| EP | 1198580 | 4/2002 |
| EP | 2024003 | 2/2009 |
| EP | 2250250 | 11/2010 |
| JP | H2-195969 | 8/1990 |

(Continued)

OTHER PUBLICATIONS

Aaron, R.K., et al., "Stimulation of experimental endochondral ossification by low-energy pulsing electromagnetic fields," *J. Bone Miner. Res.*, Nov. 2, 1989, 4, 227-233.

Aaron, R.K., et al., "The conservative treatment of osteonecrosis of the femoral head," *Clin. Orthop.*, Dec. 1989, 249, 209-218.

Ala-aho, et al., "Targeted inhibition of human collagenase-3 (MMP-13) expression inhibits squamous cell carcinoma growth in vivo," *Oncogene*, Jul. 2004, 23, 5111-5123.

(Continued)

*Primary Examiner* — Jim Ketter
(74) *Attorney, Agent, or Firm* — Woodcock Washburn, LLP (57) ABSTRACT

Methods and devices are described for the regulation of BMP 2 and 4, TGF-beta 1, 2, and 3, FGF-2, osteocalcin, and alkaline phosphatase mRNA in stem cells via capacitive coupling or inductive coupling of specific and selective electric and/or electromagnetic fields to the bone cells or other tissues containing the stem cells, where the specific and selective fields are generated by application of specific and selective signals to field generating devices disposed with respect to the stem cells so as to facilitate the treatment of diseased or injured bone and other tissues. The resulting methods and devices are useful for the targeted treatment of osteoporosis, osteopenia, osteonecrosis, fresh bone fractures, fractures at risk, non-union, bone defects, spine fusion, and/or other conditions in which BMP 2 and 4, TGF-beta 1, 2, and 3, FGF-2, osteocalcin, and alkaline phosphatase mRNA and/or protein deficiencies in stem cells has been implicated.

19 Claims, 5 Drawing Sheets

U.S. PATENT DOCUMENTS

| | | |
|---|---|---|
| 2002/0052634 A1 | 5/2002 | March |
| 2002/0125769 A1 | 9/2002 | Riley et al. |
| 2003/0211084 A1 | 11/2003 | Brighton et al. |
| 2004/0138709 A1 | 7/2004 | Brighton |
| 2005/0010264 A1 | 1/2005 | Brighton |
| 2005/0049640 A1 | 3/2005 | Gurtner et al. |
| 2005/0084962 A1 | 4/2005 | Bruce |
| 2005/0203591 A1 | 9/2005 | Brighton |
| 2006/0190043 A1 | 8/2006 | Brighton et al. |
| 2006/0235473 A1 | 10/2006 | Brighton |
| 2007/0299472 A1 | 12/2007 | Brighton |
| 2008/0269838 A1 | 10/2008 | Brighton et al. |
| 2012/0016442 A1 | 1/2012 | Brighton et al. |

FOREIGN PATENT DOCUMENTS

| | | |
|---|---|---|
| JP | 2009-538694 | 11/2009 |
| RU | 2147895 | 4/2000 |
| WO | WO 00/02585 | 1/2000 |
| WO | WO 01/62336 | 8/2001 |
| WO | WO 2004/029210 | 4/2004 |
| WO | WO 2004/033644 | 4/2004 |
| WO | WO 2005/002667 | 1/2005 |
| WO | WO 2005/070136 | 8/2005 |
| WO | WO 2007/142901 | 12/2007 |
| WO | WO 2008/109101 | 9/2008 |
| WO | WO 2009/100048 | 8/2009 |

OTHER PUBLICATIONS

Bassett, C.A.L., et al., "Effects of pulsed electromagnetic fields on Steinberg ratings of femoral head osteonecrosis," Clin. Orthop., Sep. 1989, 246, 172-185.

Bassett, C.A.L., et al., "Fundamental and practical aspects of therapeutic uses of pulsed electromagnetic fields (PEMSs)," Crit. Rev. Biomed. Eng., 1989, 17(5), 451-529.

Bassett, C.A.L., et al., "Pulsing electromagnetic field treatment in ununited fractures and failed arthrodeses," JAMA, Feb. 5, 1982, 247(5), 623-628.

Bassett,C.A.L., "Low energy pulsing electromagnetic fields modify biomedical processes," BioEssays, Jan. 1987, 6(1), 36-42.

Binder, A., et al., "Pulsed electromagnetic field therapy of persistent rotator cuff tendonitis," Lancet, Mar. 31, 1984, 695-698.

Brighton, C., et al., "Up-regulation of matrix in bovine articular cartilage explants by electric fields," Biochem. Biophys. Res. Commun., Apr. 2006, 342(2), 556-561.

Brighton, C.T., et al., "A multicenter study of the treatment of nonunion with constant direct current," J. Bone and Joint Surgery, Jan. 1981, 62-A(1), 2-13.

Brighton, C.T., et al., "Fracture healing in the rabbit fibula when subjected to various capacitively coupled electrical fields," J. Orthop. Res., 1985, 3, 331-340.

Brighton, C.T., et al., "In vitro bone-cell response to a capacitively coupled electrical field," Clin. Orthop. Related Res., Dec. 1992, 285, 255-262.

Brighton, C.T., et al., "Increased cAMP production after short-term capacitively coupled stimulation in bovine growth plate chondrocytes," J. Orthop. Res., Jul. 1988, 6, 552-558.

Brighton, C.T. et al., "Prevention and Treatment of sciatic denervation disuse osteoporosis in rat tibia with capacitively coupled electrical stimulation," Bone, 1985, 6, 87-97.

Brighton, C.T., et al., "Signal transduction in electrically stimulated bone cells," J. Bone Joint Surg. Am., Oct. 2001, 83-A(10), 1514-1523.

Brighton, C.T., et al., "Tibial nonunion treated with direct current, capactitive coupling, or bone graft," Clin. of Orthop. and related Res., Dec. 1995, 321, 223-234.

Brighton, C.T., et al., "Treatment of castration-induced osteoporosis by a capacitively coupled electrical signal in rat vertebrae," J. Bone and Joint Surgery, Feb. 1989, 71-A(2), 228-236.

Brighton, C.T., et al., "Treatment of denervation/disuse osteoporosis in the rat with a capacitively coupled electrical signal: effects on bone formation and bone resorption," J. Orthop. Res., Sep. 1988, 6, 676-684.

Brighton, C.T., et al., "Treatment of nonunion of the tibia with a capacitively coupled electrical filed," J. of Trauma, Feb. 1984, 24(2), 153-155.

Brighton, C.T., et al., "Treatment of recalcitrant non-union with a capacitively coupled electrical field," J. Bone and Joint Surgery, Apr. 1985, 67-A(4), 577-585.

Carter et al., "Theoretical determination of the current density distributions in human vertebral bodies during electrical stimulation," IEEE Trans Biomed Eng., Jun. 1990, 37(6), 606-614.

Carter, E.L., et al., "Field distributions in vertebral bodies of the rat during electrical stimulation: a parametric study," IEEE Trans. on Biomed. Eng., Mar. 1989, 36(3), 333-345.

Goodman, R., et al., "Exposure of salivary gland cells to low-frequency electromagnetic fields alters polypeptide synthesis," Proc. Natl. Acad. Sci. USA, Jun. 1988, 85, 3928-3932.

Goodwin, C.B., et al., "A double-blind study of capacitively coupled electrical stimulation as an adjunct to lumbar spinal fusions," Spine, Jul. 1999, 24(13), 1349-1356.

Grodzinsky, A.J., "Electromechanical and physicochemical properties of connective tissue," Crit. Rev. Biomed. Engng., 1983, 9(2), 133-198.

Harrison, M.H.M., et al., "Use of pulsed electromagnetic fields in perthes disease: report of a pilot study," J. Pediatr. Orthop., Sep. 1984, 4, 579-584.

Heermeier, K., et al., "Effects of extremely low frequency electromagnectic field (EMF) on collagen type 1mRNA expression and extracellular matrix synthesis of human osteoblatic cells," Bioelectromagnietcs, 1998, 19(4), 222-231.

Jiang, X., et al., "siRNA mediated inhibition of MMP-1 reduces invasive potential of a human chondrosarcoma cell line," J. of Cellular Physiology, Mar. 2005, 202, 723-730.

Jones, D.B., et al., "PEMF effects on differentiation and division in mirine melanoma cells are mediated indirectly through cAMP," Trans. BRAGS 6, 1986, 51.

Lorich, D.G., et al., "Biochemical pathway mediating the response of bone cells to capacitive coupling," Clin. Orthop. and Related Res., May 1998, 350, 246-256.

Massaro, L., et al., "Osteoarthritis of the knee joint: an eight year prospective study," Ann Rheum Dis., Nov. 1989, 48, 893-897.

Mooney, V., "A randomized double-blind prospective study of the efficacy of pulsed electromagnetic fields for inter body lumbar fusions," Spine, Jul. 1990, 15(7), 708-712.

Norton, L.A., et al., "Pulsed electromagnetic fields alter phenotypic expression in chondroblasts in tissue culture," J. Orthop. Res., Sep. 1988, 6, 685-689.

Pezzetti, F., et al., "Effects of pulsed electromagnetic fields on human chondrocytes: and in vitro study," calcify Tissue Int., Nov. 1999, 65(5), 396-401.

Pienkowski, D,. et al. "Low-power electromagnetic stimulation of osteotomized rabbit fibulae," J. of Bone & Joint Surgery, Apr. 1994, 76-A(4), 489-501.

Rodan, G.A. et al., "DNA synthesis in cartilage cells is stimulated by oscillating electric fields," Science, Feb. 10, 1978, 199, 690-692.

Ryaby, J.T., et al., "Pulsing electromagnetic fields affect the phosphorylation and expression of oncogene proteins," Trans. BRAGS 6, 1986, p. 78.

Ryaby, J.T., et al., "The effect of electromagnetic fields on protein phosphorylation and synthesis in murine melanoma cells," Trans. BRAGS, 1986, p. 32.

Wang, W., et al., "The increased level of PDGF-A constributes to the increased proliferation induced by mechanical stimulation in osteoblastic cells," Biochem. and Molecular Biol. International, Oct. 1997, 43(2), 339-346.

Wang, W., et al., "Up-regulation of chondrocyte matrix genes and products by electric fields," Clin. Orthopaedics & Related Res., Oct. 2004, 427S, S163-S173.

Wang, Z., et al., "Up-Regulation of Bone Morphogenetic Proteins in Cultured Murine Bone Cells with Use of Specific Electric Fields," Journal of Bone & Joint Surgery, May 2006, 88(5), 1053-1065.

Zhuang, H., et al., "Electrical Stimulation Induces the Level of TGF-$\beta 1$ mRNA in osteoblastic cells by a mechanism involving calcium/calmodulin pathway," Biocham. Biophys. Res. Commun., Aug. 1997, 237(2), 225-229.

Zhuang, H., et al., "Mechanical strain-induced proliferation of osteoblastic cells parallels increased TGF-$\beta 1$ mRNA,"Biochem. Biophys. Res. Commun., Dec. 1996, 229, 449-453.

\* cited by examiner

REGULATION OF STEM CELL GENE PRODUCTION WITH SPECIFIC AND SELECTIVE ELECTRIC AND ELECTROMAGNETIC FIELDS

CROSS-REFERENCE TO RELATED APPLICATIONS

The present patent application is a Continuation-in-Part of U.S. patent application Ser. No. 13/242,606 filed Sep. 23, 2011, which is a continuation of U.S. patent application Ser. No. 12/167,283 filed Jul. 3, 2008 (now U.S. Pat. No. 8,065,015), which is a continuation of U.S. patent application Ser. No. 10/257,126 filed Oct. 8, 2002 (now U.S. Pat. No. 7,465,566), which is a U.S. National Phase of PCT/US01/05991 filed Feb. 23, 2001, which claims priority to U.S. Provisional Application No. 60/184,491 filed Feb. 23, 2000. The contents of these applications are hereby incorporated by reference in their entireties.

FIELD OF THE INVENTION

The present invention is directed to a method of up-regulating the expression of those genes in stem cells that can be induced to regulate bone and cartilage growth and repair by application of an appropriate electric or electromagnetic field. The genes include bone morphogenetic genes (BMPs 2 and 4 in particular), transforming growth factor beta genes (TGF-beta 1, 2, and 3), fibroblastic growth factor-2 (FGF-2), and the genes controlling alkaline phosphatase and osteocalcin expression in living stem cells. The electric and electromagnetic fields generated by the application of specific and selective electric and electromagnetic signals to coils, electrodes, or other field generating devices are applied to injured or diseased bone, cartilage, and other tissues for treatment.

BACKGROUND OF THE INVENTION

Although there has recently been much research on the interactions and activity regarding the growth and repair of certain tissues and cells, there has been little to no research on the effect of electric and/or electromagnetic fields on stem cells and the role that such stimulated cells might have on the growth and repair of bone, cartilage, and other tissues. Such research may be useful in the development of new treatments for a variety of medical problems.

The BMP family of genes include growth factors that are important in the promotion of bone formation and maintenance, from proliferation of pre-osteoblasts, to differentiation of pre-osteoblasts to mature osteoblasts, and to maintenance of the osteoblast throughout its life span. Transforming growth factors (TGF-beta 1, 2 and 3) control many cellular functions including growth, proliferation and differentiation. Fibroblastic growth factor (FGF-2) has been shown to have a positive anabolic effect on bone formation in intact animals and to reduce bone loss in experimental models of osteoporosis. FGF-2 (also termed basic fibroblastic growth or bFGF) stimulates bone formation, decreases osteoclast surfaces, and induces new bone spicules within the marrow cavity of bone.

Thus, up-regulation of the genes discussed above would be useful in the treatment of the disease commonly known as osteoporosis, where bone demineralizes and becomes abnormally rarefied. In osteoporosis, bone resorption exceeds bone formation, leading to bone weakening and possible vertebral body fracture and collapse. While osteoporosis is generally thought to afflict the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, and such bone loss may ultimately lead to a secondary fracture in an already osteoporotic skeleton. Diminished bone density may lead not only to vertebrae collapse, but also to fractures of hips, lower arms, wrists, ankles as well as incapacitating pains. Alternative non-surgical therapies to induce bone formation in such diseases are needed.

Pulsed electromagnetic fields (PEMF) and capacitive coupling (CC) have been used widely to treat nonhealing fractures (nonunion) and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. PEMFs generate small, induced currents (Faraday currents) in the highly-conductive extracellular fluid, while capacitive coupling directly causes currents in the tissues; both PEMFs and CC thereby mimic endogenous electrical currents.

The endogenous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in bone have demonstrated a mechanical-electrical transduction mechanism that appears when bone is mechanically compressed, causing movement of fluid and electrolytes over the surface of fixed negative charges on the surface of bone cells, thus producing streaming potentials. These electrical potentials serve a purpose in bone, and, along with mechanical strain, lead to signal transduction that is capable of stimulating bone cell synthesis of a calcifiable matrix, and, hence, the formation of bone.

It was reported in 1996 by the present inventor and others that a cyclic biaxial 0.17% mechanical strain produces a significant increase in TGF-$\beta_1$ mRNA in cultured MC3T3-E1 bone cells in a Cooper dish (Brighton et al., *Biochem. Biophys. Res. Commun.* 229: 449-453, 1996). Several significant studies followed in 1997. In one study it was reported that the same cyclic biaxial 0.17% mechanical strain produced a significant increase in PDGF-A mRNA in similar bone cells (Brighton et al., *Biochem. Biophys. Res. Commun.* 43: 339-346, 1997). It was also reported that a 60 kHz capacitively coupled electric field of 20 mV/cm produced a significant increase in TGF-$\beta_1$ in similar bone cells in a Cooper dish (Brighton et al., *Biochem. Biophys. Res. Commun.* 237: 225-229, 1997). It has also been reported that chondrocyte matrix genes and proteins can be up-regulated by specific and selective electric fields (Wang, W., Wang, Z., Zhang, G., Clark, C. C., and Brighton, C. T., *Clin. Orthp. and Related Res.*, 427S: S163-173, 2004; Brighton, C. T., Wang, W., and Clark, CC, *Biochem. Biophys. Res. Commun.*, 342: 556-561, 2006). Further, it has been shown that the gene expression of bone morphogenetic proteins (BMPs) can also be up-regulated by specific and selective electric fields that differ from the electric fields in various signal aspects from those signals that are specific and selective for articular cartilage (Wang, Z., Clark, C. C. and Brighton, C. T., *J. Bone Joint Surg.*, 88: 1053-1065, 2006).

In U.S. Pat. No. 7,465,566 to the present inventor, methods were disclosed for determining the specific and selective electrical and electromagnetic signals for use in creating fields for regulating target genes of diseased or injured tissues. The present invention builds upon the techniques described therein by describing the method of regulating expression of the targeted genes in bone marrow stem cells. These genes belong to the BMP super family, and include BMP 2 and 4, FGF-2, and TGF-beta 1, 2, 3, alkaline phosphatase, and osteocalcin. Through application of a field generated by a specific and selective electrical and electromagnetic signal, the treatment of bone diseases and injuries including osteoporosis, osteopenia, osteonecrosis, bone defects, fresh fractures, fractures at risk, delayed union, nonunion, and as an adjunct in spinal fusion is described.

SUMMARY OF THE INVENTION

The present invention relates to regulating the gene expression of the BMP super family including, but not limited to, BMP 2 and 4, TGF beta 1, 2, and 3, and fibroblastic growth factor-2 (FGF-2), alkaline phosphatase, and osteocalcin in stem cells (as an example) via the application of specific and selective electric and/or electromagnetic fields generated by the application of specific and selective signals to coils, electrodes, or other field generating devices adjacent the bone or tissue cells of interest. By performing sequential dose-response curves on the signal duration, amplitude, frequency, and duty cycle in which the effects of the resultant electric field are measured, the optimal signal for up-regulating mRNA in stem cells was discovered. The optimal signal generated a capacitively coupled electric field with an amplitude of 20-40 mV/cm, a duration of 12 hours, a frequency of 60 kHz, and a duty cycle of 50-100%. In particular, the present invention relates to up-regulating the gene expression in stem cells via the application of fields generated by such signals.

In an exemplary embodiment of the invention, methods are provided to specifically and selectively up-regulate the gene expression of stem cells mentioned above (as measured by mRNA) with capacitively coupled electric fields, electromagnetic fields, or combined fields. Osteoporosis, osteopenia, osteonecrosis, fresh fractures, fractures at risk, delayed unions, nonunion fractures, bone defects, as an adjunct in spinal fusion and the like are treated with a capacitively coupled electric field of about 10-40 mV/cm with a field duration of about 12 hours, a frequency of 60 kHz, a duty cycle of 50%-100%, and a sine wave configuration that causes the expression of BMP 2 and 4, FGF-2, and TGF beta 1, 2, and 3 to be up-regulated. In accordance with the method of the invention, a "specific and selective" signal is a signal that has predetermined characteristics of amplitude, duration, duty-cycle, frequency, and waveform that up-regulates the expression of the BMP super family of genes (specificity). This allows one to choose different signals to up-regulate the expressions of the genes in the BMP super family in order to achieve a given biological or therapeutic response (selectivity). The invention further relates to devices employing the methods described herein to generate specific and selective signals that create electric and/or electromagnetic fields to up-regulate the expression of the BMP super family of genes.

In related aspects, the invention relates to methods and devices for the treatment of osteoporosis, osteopenia, osteonecrosis, fresh fractures, fractures at risk, delayed unions, nonunion fractures, bone defects, as an adjunct in spinal fusion and other therapies treating one or more of the above conditions. The method of the invention also includes the methodology for determining the "specific and selective" signal for BMP 2 and 4, TGF beta-1, 2, and 3 and FGF-2 gene expression by methodically varying the duration of a starting signal known to increase, or suspected to increase, cellular production of the stated genes of interest. After finding the optimal duration, the amplitude of the signal is varied for the optimal duration of time as determined by the gene expression of the above stated genes. The duty cycle, frequency, and waveform are varied methodically in the same dose response manner while keeping the other signal characteristics constant. This process is repeated until the optimal signal is determined that produces the greatest increase in the expression of BMP 2 and 4, TGF beta-1, 2, and 3, FGF-2, alkaline phosphatase, and osteocalcin. The optimal signal for each of the stated genes may differ from one gene to another.

These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which.

DETAILED DESCRIPTION OF ILLUSTRATIVE EMBODIMENTS

The invention will be described in detail below with reference to FIGS. 1-5. Those skilled in the art will appreciate that the description given herein with respect to those figures is for exemplary purposes only and is not intended in any way to limit the scope of the invention. All questions regarding the scope of the invention may be resolved by referring to the appended claims.

The present invention is based on the discovery that the expression of certain stem cell genes can be regulated by the application of fields generated by specific and selective electric and/or electromagnetic signals applied to coils, electrodes, or other field generating devices in the vicinity of the genes. In other words, it has been discovered by the present inventor that there is a specific electric and/or electromagnetic signal that generates a field for regulating genes in stem cells in bone, cartilage and other tissues and that these specific signals are capable of specifically and selectively regulating the genes in such cells. In particular, gene expression governing the growth, maintenance, repair, and degeneration or deterioration of tissues or cells can be regulated in accordance with the invention via the application of fields generated by application of specific and selective electric and/or electromagnetic signals to field generating devices so as to produce a salutary clinical effect. Such discoveries are useful in the development of treatment methods that target certain medical conditions including osteoporosis, osteopenia, osteonecrosis, fresh bone fractures, fractures at risk, delayed union, non-union, bone defects, spine fusion, and as an adjunct in the treatment of any one or more of the above conditions.

As used herein, the phrase "signal" is used to refer to a variety of signals including mechanical signals, ultrasound signals, electromagnetic signals and electric signals output by a device. It is to be understood that the term "field" as used herein refers to an electrical field within targeted tissue, whether it is a combined field or a pulsed electromagnetic field or generated by direct current, capacitive coupling or inductive coupling.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance from a tissue or a cell, or from a source outside of or external to the body.

The phrase "specific and selective" signal means a signal that produces an electric field that has predetermined characteristics of amplitude, duration, duty cycle, frequency, and waveform that up-regulate or down-regulate a targeted gene or targeted functionally complementary genes (specificity). This allows one to choose different "specific and selective" signals to up-regulate or down-regulate expression of various genes in order to achieve a given biological or therapeutic response (selectivity).

The term "regulate" means to control gene expression. Regulate is understood to include both up-regulate and down-regulate. Up-regulate means to increase expression of a gene, while down-regulate means to inhibit or prevent expression of a gene.

"Functionally complementary" refers to two or more genes whose expressions are complementary or synergistic in a given cell or tissue.

"Tissue" refers to an aggregate of cells together with their extracellular substances that form one of the structural materials of a patient. As used herein, the term "tissue" is intended to include any tissue of the body including muscle and organ tissue, tumor tissue, as well as bone or cartilage tissue. Also, the term "tissue" as used herein may also refer to an individual cell.

"Patient" refers to an animal, preferably a mammal, more preferably a human.

The present invention provides treatment methods and devices that target certain tissues, cells or diseases. In particular, the gene expression associated with the repair process in injured or diseased tissues or cells can be regulated by the application of fields generated by electric signals that are specific and selective for the genes to be regulated in the target tissues or cells. Gene expression can be up-regulated or down-regulated by the application of signals that are specific and selective for each gene or each set of complementary genes so as to produce a beneficial clinical effect. For example, a particular specific and selective signal may create an electric field that up-regulates a certain desirable gene expression, while the same or another particular specific and selective signal may create an electric field that down-regulates a certain undesirable gene expression. A certain gene may be up-regulated by a field generated by one particular specific and selective signal and down-regulated by a field generated by another specific and selective signal. Those skilled in the art will understand that certain diseased or injured tissues can be targeted for treatment by regulating those genes governing the growth, maintenance, repair, and degeneration or deterioration of the tissues.

The methods and devices of the present invention are based on identifying those signals that generate fields that are specific and selective for the gene expression associated with certain targeted diseased or injured tissue. For example, fields of electricity applied in various forms (e.g., capacitive coupling, inductive coupling, or combined fields) can specifically and selectively regulate gene expression in targeted tissues or cells in a patient's body by varying the frequency, amplitude, waveform or duty cycle of the signal applied to the field generating device for generation of the applied field for each selected gene or family of genes. The duration of time exposed to electric field can also influence the capability of the electric field to specifically and selectively regulate gene expression in targeted tissues or cells in a patient's body. Specific and selective signals may generate electric fields for application to each gene systematically until the proper combination of frequency, amplitude, waveform, duty cycle, and duration is found that provides the desired effect on gene expression.

It is to be understood that a variety of diseased or injured tissues or disease states can be targeted for treatment because the specificity and selectivity of an electric field for a certain gene expression can be influenced by several factors. In particular, an electrical field generated from an electrical signal having the appropriate frequency, amplitude, waveform and/or duty cycle can be specific and selective for the expression of certain genes and thus provide for targeted treatments. Temporal factors (e.g., duration of time exposed to the electrical field) can also influence the specificity and selectivity of an electric field for a particular gene expression. The regulation of gene expression may be more effective (or made possible) via the application of an electrical field for a particular duration of time. Therefore, those skilled in the art will understand that the present invention provides for varying the frequency, amplitude, waveform, duty cycle and/or duration of application of an electric signal that generates an electric field until the electric field is found to be specific and selective for certain gene expressions in order to provide for treatments targeting a variety of diseased or injured tissue or diseases.

Thus, the present invention can provide for targeted treatments because it is possible to regulate expression of certain genes associated with a particular diseased or injured tissue via the application of electric fields generated by specific and selective signals of appropriate frequency, amplitude, waveform and/or duty cycle for an appropriate duration of time.

The specificity and selectivity of a signal generating an electrical field may thus be influenced so as to regulate the expression of certain genes in order to target certain diseased or injured tissue or disease states for treatment. In particular, the present invention provides for the targeted treatment of osteoporosis, osteopenia, osteonecrosis, fresh bone fractures, fractures at risk, nonunion, bone defects, spine fusion, and as an adjunct in the treatment of one or any of the above conditions.

Figure 5:
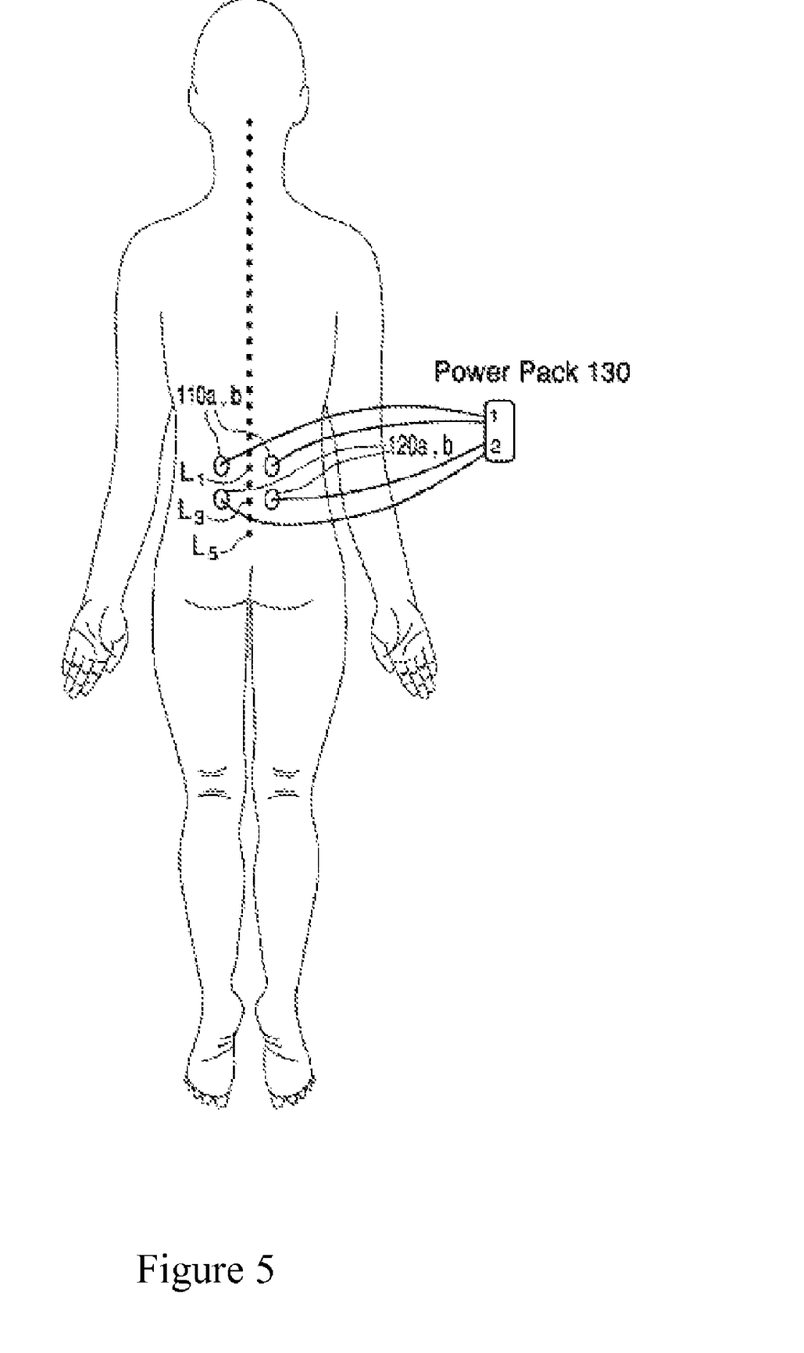
FIG. 5 is a diagram illustrating a device for the treatment of osteoporosis of the spine, for example, in accordance with an exemplary application of the present invention.

The devices of the present invention are capable of applying specific and selective signals to a field generating device for the generation of a specific and selective field that is applied directly to diseased or injured tissue and/or to the skin of a patient. The devices of the present invention may also provide for the remote application of specific and selective fields (e.g., application of a field at a distance from diseased or injured tissue yet which yields the desired effect within the targeted cells), although it will be appreciated that capacitively coupled devices must touch the subject's skin. The devices of the present invention may include means for attaching the electrodes to the body of a patient in the vicinity of injured or diseased tissue in the case of capacitive coupling. For example, self-adherent conductive electrodes may be attached to the skin of the patient on both sides of a fractured bone. As shown in FIG. 5, the device of the present invention may include self-adherent electrodes for attaching the device to the body of a patient. For example, the device of the present invention may include electrodes attached to a power unit that has a VELCRO® patch on the reverse side such that the power unit can be attached to a VELCRO® strap (not shown) fitted around a cast on the patient. In the case of inductive coupling, the device of the present invention may include coils or other field generating device attached to a power unit in place of electrodes. The self-adherent strip electrodes also may be attached to the back of a patient, with each electrode of a pair of electrodes running parallel to the spine, with one electrode of the pair of electrodes placed longitudinally on one side of the spine and the other electrode of the pair placed longitudinally on the opposite side of the spine. In this case, the VELCRO® patch may be part of a garment worn by the patient.

The device of the present invention can be employed in a variety of ways. The device may be portable or may be temporarily or permanently attached to a patient's body. The device of the present invention is preferably non-invasive. For example, the device of the present invention may be applied to the skin of a patient by application of electrodes adapted for contact with the skin of a patient for the application of electric fields generated by the predetermined specific and selective electric signals. Such signals may also be applied via coils in which time varying currents flow, thus producing specific and selective electromagnetic fields that penetrate the tissue and create the specific and selective electric fields in the target tissue. For example, the coils may be incorporated into the patient's clothing and placed adjacent the patient's spine and/or hip as described in U.S. Pat. No. 7,158,835. The device of the present invention may also be capable of implantation in a patient, including implantation under the skin of a patient.

Those skilled in the art will further understand that the field generating devices of the present invention can be provided in a variety of forms including a capacitively coupled power unit with programmed, multiple, switchable, specific and selective signals for application to one pair or to multiple pairs of electrodes, electromagnetic coils or a solenoid attached to a power unit with switchable, multiple, specific and selective signals, and an ultrasound stimulator with a power supply for generating specific and selective signals. Generally speaking, field generating device preference is based on patient acceptance and patient compliance. The smallest and most portable unit available in the art at the present time is a capacitive coupling unit; however, patients with extremely sensitive skin may prefer to use inductive coupling units. On the other hand, ultrasound units require the most patient cooperation, but may be desirable for use by certain patients.

EXAMPLE

The invention is demonstrated in the following example, which is for purposes of illustration and is not intended to limit the scope of the present invention.

Materials and Methods

Human stem cells ($5 \times 10^5$ cells/cm$^2$) were placed onto specially-modified Cooper dishes. The cells were grown for ten days with the medium changed just prior to beginning of the experimental condition. On day 10 the experimental cell cultures throughout these studies were subjected to a capacitively coupled 60 kHz sine wave signal with an output of 44.81 V peak-to-peak. This produced a calculated-field strength in the culture medium in the dishes of 20 mV/cm with a current density of 300 µA/cm$^2$. Control cell culture dishes were identical to those of the stimulated dishes except that the electrodes were not connected to a function generator.

At the end of the experiment, total RNA was isolated using TRIzol, according to the manufacturer's instructions, and reversed transcription (RT) using SuperScript II reverse transcriptase was performed. Oligonucleotide primers to be used in the real time RT-PCR technique were selected from published cDNA sequences or designed using the Primer Express software program. Quantitative real-time analysis of RT-PCR products was performed using an ABI Prism® 7000 Sequence Detection System.

Figure 1:
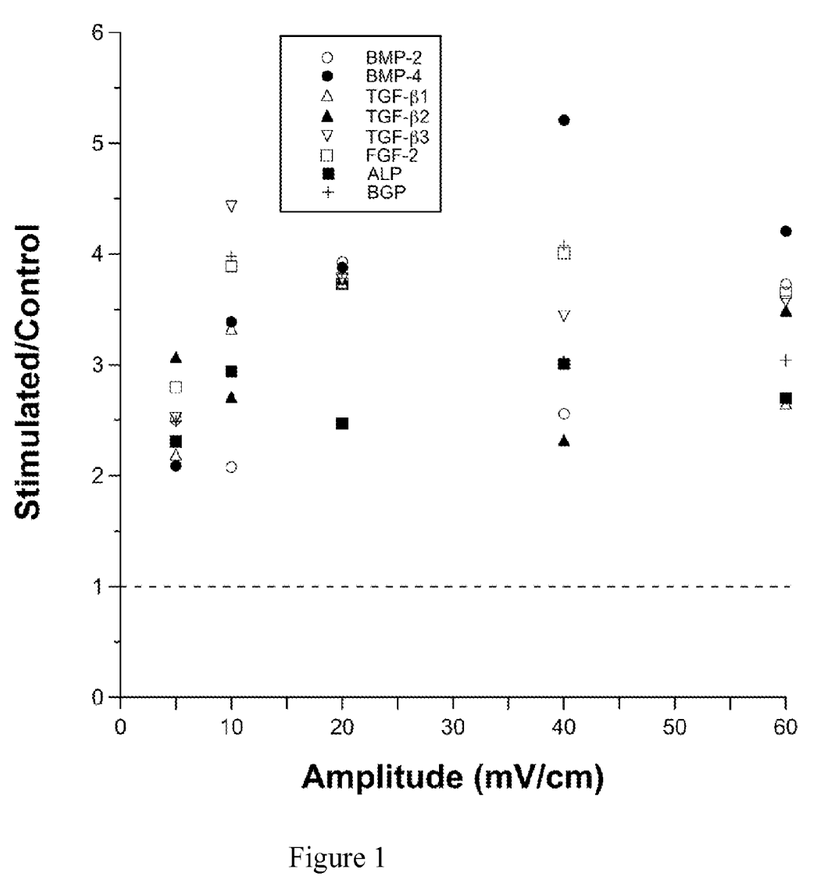
FIG. 1 is a scatter plot representation of the mRNA expression of BMPs 2 and 4, TGF I, 2, and 3, FGF-2, alkaline phosphatase, and osteocalcin when stem cells are exposed to various capacitively coupled electric field amplitudes. As indicated, the maximum expression for the various mRNAs occurred within a range of signals from 10 mV/cm to 60 mV/cm.
Figure 2:
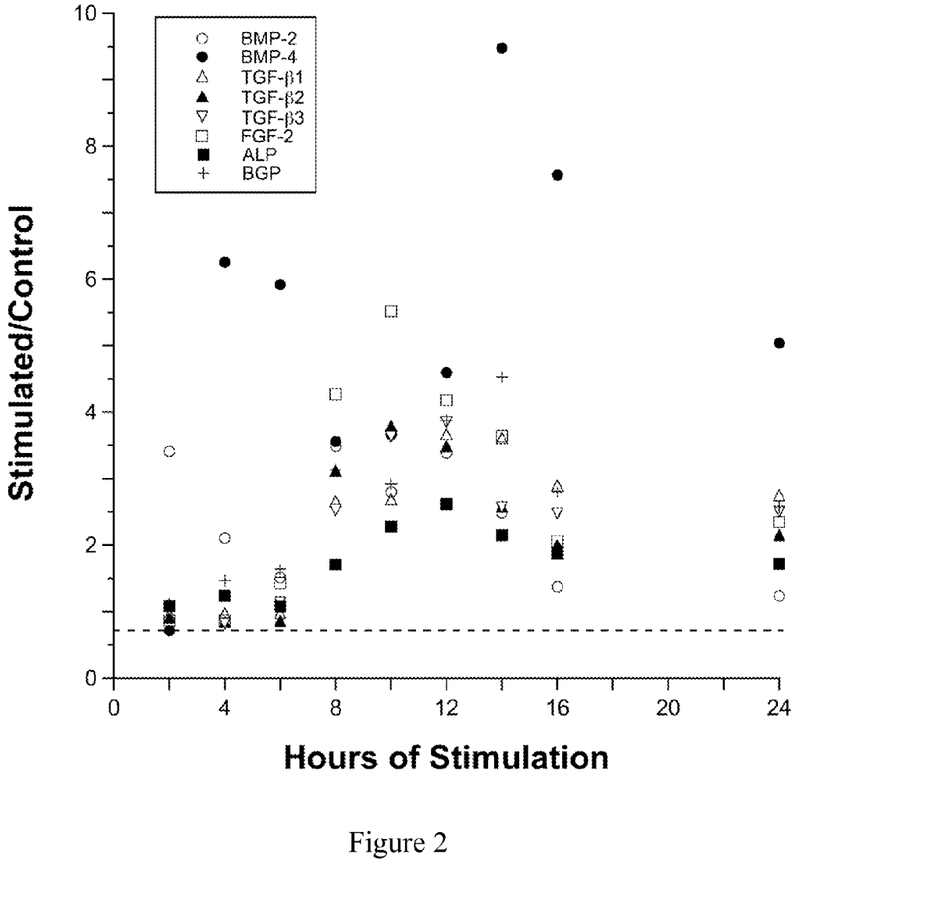
FIG. 2 is a scatter plot representation of the mRNA expression of BMPs 2 and 4, TGF I, 2, and 3, FGF-2, alkaline phosphatase, and osteocalcin when stem cells are exposed to a capacitively coupled electric field with an amplitude of 20 mV/cm for various time durations. As indicated, the maximum expression for the various mRNAs occurred with a signal duration of 12 hours.
Figure 3:
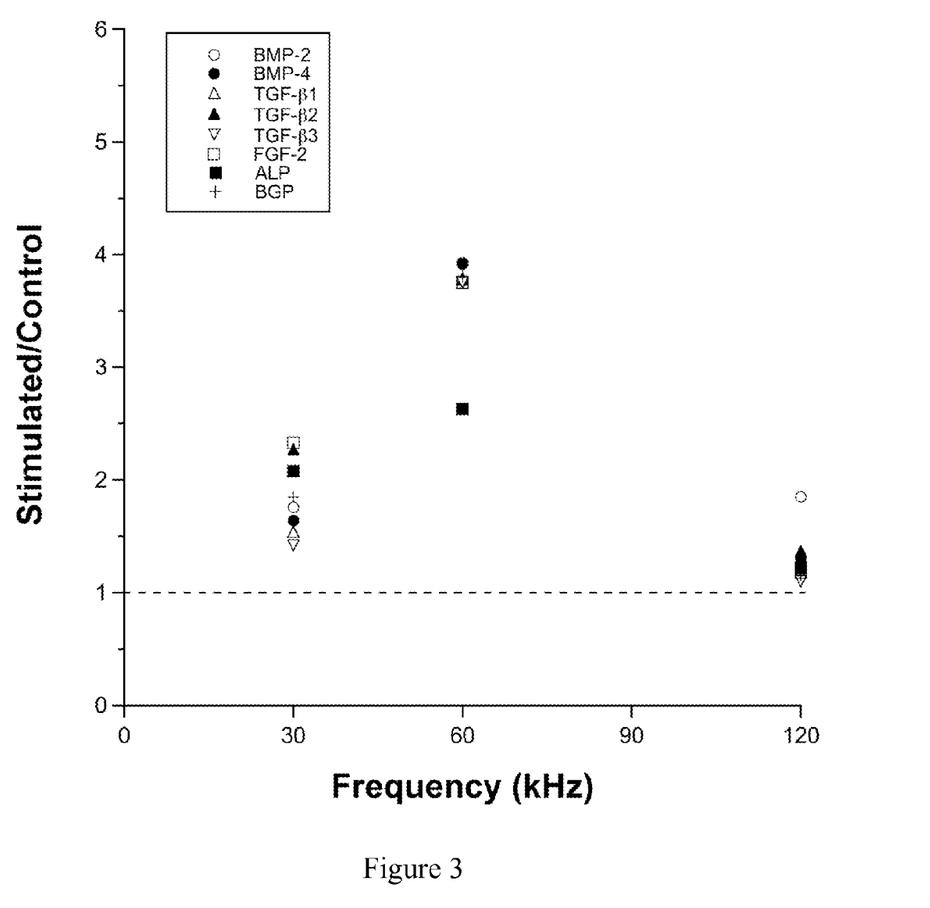
FIG. 3 is a scatter plot representation of the mRNA expression of BMPs 2 and 4, TGF I, 2, and 3, FGF-2, alkaline phosphatase, and osteocalcin when stem cells are exposed to various capacitively coupled electric field frequencies with a field amplitude of 20 mV/cm and a signal duration of 12 hours. As indicated, the maximum expression for the various mRNAs occurred with a frequency of 60 kHz.
Figure 4:
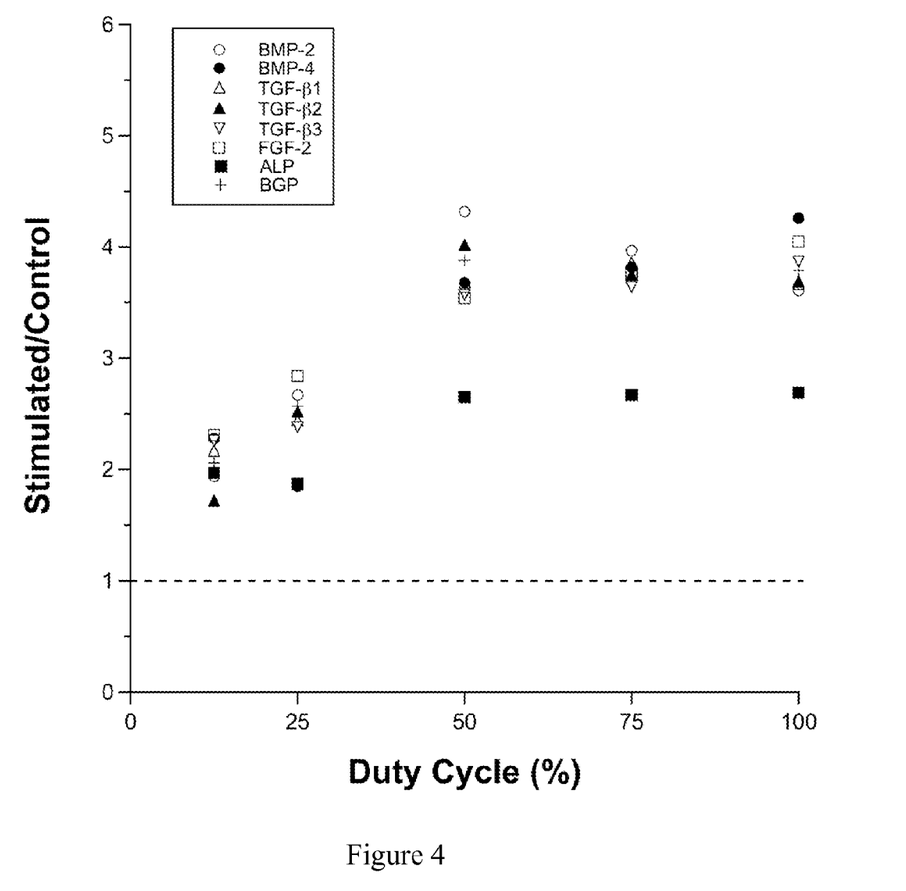
FIG. 4 is a scatter plot representation of the mRNA expression of BMPs 2 and 4, TGF I, 2, and 3, FGF-2, alkaline phosphatase, and osteocalcin when stem cells are exposed to various capacitively coupled electric field duty cycles with a frequency of 60 kHz, a field amplitude of 20 mV/cm, and a signal duration of 12 hours. As indicated, the maximum expression for the various mRNAs occurred with a 50% to 100% duty cycle with a sine wave configuration.

The optimal signal for the desired up-regulation of the genes of interest, including BMP 2 and 4, TGF-beta 1, 2, and 3, FGF-2, alkaline phosphatase (ALP), and osteocalcin (BGP), was found systematically as follows. An electrical signal known to cause creation of an electric field that increases (or even just suspected to increase) cellular production of a given protein is taken as the starting signal for determining the specific signal for generating the electric field in the targeted tissue for the gene expression (mRNA) of that protein. A dose-response curve is first performed by varying the amplitude of the signal while holding all the other signal characteristics constant (duration, duty cycle, and frequency) (FIG. 1). This determines the optimal amplitude of the starting signal for the gene expression of that protein. A second dose-response curve is then performed, this time varying the duration of the electric field in the targeted tissue (in mV/cm) while holding the optimal amplitude and other signal characteristics constant (FIG. 2). A third dose response is performed, this time varying the signal frequency while holding constant the optimal amplitude and optimal duration as found previously (FIG. 3). A fourth dose-response is performed varying the duty cycle from 100% (constant) to 10% or less while holding constant the optimal amplitude, duration, and frequency as found previously (FIG. 4). By this method, an optimal signal is determined for producing the greatest increase in the gene expression of BMP 2 and 4, TGF-beta 1, 2, and 3, FGF-2, alkaline phosphatase, and osteocalcin.

FIG. 1 illustrates a scatter plot of human stem cell response after 10 days of culture showing the effect of amplitude of stimulation on mRNA expression of the eight genes of interest (BMP 2 and 4, TGF-beta 1, 2, and 3, FGF-2, alkaline phosphates, and osteocalcin). At 20 mV/cm there is convergence of mRNA expression for seven of the genes that is not present at the other amplitude levels. It is further noted that the selected genes can give specific responses. For example, the optimal amplitude for TGF-beta 3 occurs at 10 mV/cm, BMP-4 at 60 mV/cm, etc. The stem cells were stimulated for 12 hours at a frequency of 60 KHz at a 50% duty cycle.

FIG. 2 illustrates a scatter plot of human stem cell response after 10 days of culture showing the effect of duration of stimulation on mRNA expression of the eight genes of interest (BMP 2 and 4, TGF-beta 1, 2, and 3, FGF-2, alkaline phosphates, and osteocalcin). The stem cells were stimulated for 2 to 24 hours with a signal frequency of 60 KHz, a duty cycle of 50%, and an amplitude of 20 mV/cm. It is noted that after 12 hours of stimulation there was a convergence of the eight gene expressions that is lacking at the other time periods tested. Also, as in FIG. 1, selected genes have an optimal response at specific hours other than at 12 hours of stimulation.

FIG. 3 illustrates a scatter plot of human stem cell response after 10 days of culture showing effect of frequency of stimulation on mRNA expression of the eight genes of interest (BMP 2 and 4, TGF-beta 1, 2, and 3, FGF-2, alkaline phosphates, and osteocalcin). The stem cells were stimulated for the various signal frequencies at a duty cycle of 50%, and an amplitude of 20 mV/cm. It is noted that after 12 hours of stimulation there were optimal expressions of the eight genes at a frequency of 60 kHz.

FIG. 4 illustrates a scatter plot of human stem cell response after 10 days of culture showing the effect of the duty cycle on stimulation of mRNA expression of the eight genes of interest (BMP 2 and 4, TGF-beta 1, 2, and 3, FGF-2, alkaline phosphates, and osteocalcin). The duty cycles were 12.5% (1 minute on/7 minutes off), 25% (1 minute on/3 minutes off), 50% (1 minute on/1 minute off), 75% (1 minute on/20 seconds off), and 100% (signal always on). It is noted that 50, 75, and 100% give virtually identical results. A 50% duty cycle is chosen since it requires less energy, and hence, gives longer battery life.

FIG. 5 illustrates a patient being treated for osteoporosis with a capacitive coupling device. The power pack (130) is worn in a cloth pocket bag that is held at the waist with a cloth belt or can be slipped into any pocket in the patient's clothing. Elements 110a,b and 120a,b indicate surface conductive cloth electrodes that are adherent to the patient's back with conductive gel on either side of the lumbar spine at the L1 to the L5 levels. The power unit delivers an optimized signal in accordance with the invention, e.g., a 20 mV/cm sine wave signal at a frequency of 60 KHz, a duty cycle of 50%, and for a duration of 12 hours per day. This is the optimal signal for stimulating the stem cells within the designated lumbar vertebrae for up-regulating mRNA expression of the eight genes of interest (BMP 2 and 4, TGF-beta 1, 2, and 3, FGF-2, alkaline phosphates, and osteocalcin).

The present invention clearly shows that the optimal electric field described in the example (10 mV/cm-60 mV/cm, preferably 20 mV/cm, 12 hours duration, 60 kHz frequency, and 50-100% duty cycle) can significantly up-regulate BMP 2 and 4, TGF-beta 1, 2, and 3, FGF-2, alkaline phosphatase, and osteocalcin and osteocalcin and, hence, increase bone formation in osteoporosis, osteopenia, osteonecrosis, bone fractures, fractures at risk, nonunion, bone defects, spine fusion, and as an adjunct in the treatment of one or any of the above. Also, FIGS. 1-4 clearly show that there are differences among the responses of the various genes in each of the four dose-response studies. Those skilled in the art will appreciate that an appropriate electric field, as described herein with capacitive coupling, is also equally effective with inductive coupling and all electromagnetic systems that produce equivalent, or nearly equivalent, electric field characteristics. Those skilled in the art will also appreciate that more unique signal characteristics may be discovered through more experimentation with more data points (e.g., a 100±3% duty cycle for 30±3 min), but such relatively minor variations in each of the signal characteristics are believed to be within the level of those skilled in the art given the teachings herein.

Those skilled in the art will also appreciate that numerous other modifications to the invention are possible within the scope of the invention. For example, the optimal field described herein can be applied to any bone via two or more appropriate surface electrodes, in pairs or strips, incorporated in braces, wraps, or casts, and delivered by means of capacitive coupling. Also, the optimal field described here can be applied to any bone via coil(s) or solenoid incorporated into braces, wraps, or casts, and delivered by means of inductive coupling. Accordingly, the scope of the invention is not intended to be limited to the preferred embodiment described above, but only by the appended claims.

What is claimed:
1. A method of up-regulating the gene expression of BMP 2 and 4, TGF-beta 1, 2, and 3, FGF-2, and osteocalcin and alkaline phosphatase and of increasing bone formation by human stem cells in targeted tissue, comprising the steps of:
generating at least one specific and selective signal having a frequency of approximately 60 kHz that when applied to one or more field generating devices operatively disposed with respect to said targeted tissue causes the generation of an electric and/or electromagnetic field having an amplitude of approximately 10 to 60 mV/cm in the targeted tissue that is specific and selective for the up-regulation of the gene expression of BMP 2 and 4, TGF-beta 1, 2, and 3, FGF-2, and osteocalcin and alkaline phosphatase in the targeted tissue as measured by mRNA when said field is applied to the targeted tissue containing said BMP 2 and 4, TGF-beta 1, 2, and 3, FGF-2, and osteocalcin and alkaline phosphatase; and
exposing said targeted tissue to the specific and selective field generated by said one or more field generating devices upon application of said at least one specific and selective signal thereto for a duration of approximately 12 hours per 24 hour period at a duty cycle between 50% and 100% so as to selectively up-regulate the gene expression of BMP 2 and 4, TGF-beta 1, 2, and 3, FGF-2, osteocalcin, and alkaline phosphatase as measured by mRNA in said targeted tissue as a result of exposure to said field in the targeted tissue.

2. The method of claim 1 wherein the generating step comprises the step of selectively varying the amplitude, duration, duty cycle, frequency, and waveform of the applied specific and selective signal until the gene expression of BMP 2 and 4, TGF-beta 1, 2, and 3, FGF-2, and osteocalcin and alkaline phosphatase as measured by mRNA in said targeted tissue as a result of exposure to the resultant specific and selective field in the targeted tissue is substantially increased.

3. The method of claim 1 wherein the generating step comprises the step of generating an electric signal having a sine wave configuration where the resultant specific and selective field in the targeted tissue has an amplitude of approximately 20 mV/cm.

4. The method of claim 1 wherein said generating step comprises the step of generating the specific and selective signal at a remote source and said exposing step comprises the step of applying the specific and selective field to targeted stem cell tissue.

5. The method of claim 4 wherein the exposing step comprises the step of applying the specific and selective field in the targeted tissue generated by the one or more field generating devices upon application of said at least one specific and selective signal thereto to the targeted stem cell tissue through capacitive coupling or inductive coupling.

6. The method of claim 5 wherein the specific and selective signal applied to said electrodes causes the electrodes to generate a capacitive coupling electric field, and the specific and selective signal applied to said one or more coils causes said one or more coils to generate an electromagnetic field or a combined field.

7. A method for treating conditions including osteoporosis, osteopenia, osteonecrosis, bone defects, fresh fractures, fractures at risk, delayed union, nonunion, and as an adjunct in spinal fusion, comprising:
  generating at least one specific and selective signal having a frequency of approximately 60 kHz that when applied to one or more field generating devices operatively disposed with respect to targeted tissue causes the generation of an electric and/or electromagnetic field having an amplitude of approximately 10 to 60 mV/cm in stem cells in the targeted tissue that is specific and selective for the up-regulation of the gene expression of BMP 2 and 4, TGF-beta 1, 2, and 3, FGF-2, osteocalcin, and alkaline phosphatase in the targeted tissue as measured by mRNA when said field is applied to the targeted tissue containing said BMP 2 and 4, TGF-beta 1, 2, and 3, FGF-2, osteocalcin, and alkaline phosphatase; and
  exposing said targeted tissue to the specific and selective field generated by said one or more field generating devices upon application of said at least one specific and selective signal thereto for a duration of approximately 12 hours per 24 hour period at a duty cycle between 50% and 100% so as to selectively up-regulate the gene expression of BMP 2 and 4, TGF-beta 1, 2, and 3, FGF-2, osteocalcin, and alkaline phosphatase as measured by mRNA in said targeted tissue as a result of exposure to said field in the targeted tissue.

8. The method of claim 7 wherein the exposing step comprises the step of applying either capacitively coupling or inductively coupling with a specific and selective field to the targeted tissue.

9. The method of claim 7 wherein the exposing step comprises the step of applying either an electromagnetic field or a combined field to the targeted tissue.

10. The method of claim 7 wherein the generating step comprises the step of generating an electric signal having a sine wave configuration where the resultant specific and selective field has an amplitude of approximately 20 mV/cm in the targeted tissue.

11. The method of claim 7 wherein the generating step comprises the steps of starting with any electric signal that when applied to said one or more field generating devices generates an electric and/or electromagnetic field that is known or thought to be effective on living cells, performing a first dose-response curve on the amplitude of stimulation of the field to determine an optimal amplitude; performing a second dose-response curve on the optimal duration of the applied electric signal using the optimal amplitude as previously found to determine an optimal duration; performing a third dose-response curve on the frequency of the applied electric signal keeping the optimal amplitude and optimal duration as previously found to determine an optimal frequency; performing a fourth dose-response curve varying the duty cycle of the applied electric signal and keeping the optimal amplitude, duration, and frequency as previously found to determine an optimal duty cycle, and keeping the optimal duration, amplitude, frequency and duty cycle constant while varying the wave form until an optimal wave form for the up-regulation of the gene expression of BMP 2 and 4, TGF-beta 1, 2, and 3, FGF-2, osteocalcin, and alkaline phosphatase as measured by mRNA and protein in the tissue is found.

12. A device for the treatment of osteoporosis, osteopenia, osteonecrosis, fresh bone fractures, fractures at risk, nonunion, bone defects, spine fusion, and as an adjunct in the treatment osteoporosis, osteopenia, osteonecrosis, fresh bone fractures, fractures at risk, nonunion, bone defects, spine fusion, and/or other conditions in which BMP 2 and 4, TGF-beta 1, 2, and 3, FGF-2, osteocalcin, and alkaline phosphatase as measured by mRNA and protein has been implicated in a patient, comprising:
  a signal source that generates at least one specific and selective signal having a frequency of approximately 60 kHz, said signal source controlling and varying duration of time of application of said at least one specific and selective signal for a duration of approximately 12 hours per 24 hour period and said signal source varying a duty cycle of said specific and selective signal between 50% and 100%; and
  one or more field generating devices connected to the signal source so as to receive said at least one specific and selective signal and that are operatively disposed with respect to targeted tissue, said one or more field generating devices upon receipt of said at least one specific and selective signal causing the generation of a specific and selective electric and/or electromagnetic field having an amplitude of approximately 10 to 60 mV/cm in the targeted tissue that is specific and selective for the up-regulation of the gene expressions of BMP 2 and 4, TGF-beta 1, 2, and 3, FGF-2, osteocalcin, and alkaline phosphatase and/or the up-regulation of the proteins in the targeted tissue as measured by mRNA when the field is applied to the targeted tissue containing BMP 2 and 4, TGF-beta 1, 2, and 3, FGF-2, osteocalcin, and alkaline phosphatase.

13. The device of claim 12 further comprising a portable power unit that drives said signal source.

14. The device of claim 12 further comprising means for attaching the one or more field generating devices to the body of a patient in the vicinity of targeted bone tissue.

15. The device of claim 12 further comprising means for attaching the signal source to the body of a patient.

16. The device of claim 12 wherein the field generated by application of said at least one specific and selective signal to the one or more field generating devices is applied to said targeted tissue via capacitive coupling or inductive coupling.

17. The device of claim 16 wherein the specific and selective signal has a sine wave configuration.

18. A method of determining a specific and selective signal that when applied to one or more field generating device causes the generation of a field in targeted tissue that up-regulates BMP 2 and 4, TGF-beta 1, 2, and 3, FGF-2, osteocalcin, and alkaline phosphatase in the targeted tissue, comprising the steps of starting with a starting electric signal with a signal shape and frequency that when applied to said one or more field generating devices generates an electric and/or electromagnetic field that is known or thought to affect cellular production of targeted tissue that up-regulates BMP 2 and 4, TGF-beta 1, 2, and 3, FGF-2, osteocalcin, and alkaline phosphatase mRNA, selectively varying a duration of application of said starting signal until a duration that provides a most significant increase in production of BMP 2 and 4, TGF-beta 1, 2, and 3, FGF-2, osteocalcin, and alkaline phosphatase mRNA is found, selectively varying an amplitude of the starting signal until an amplitude that provides a most significant increase in production of BMP 2 and 4, TGF-beta 1, 2, and 3, FGF-2, osteocalcin, and alkaline phosphatase mRNA is found, selectively varying a duty cycle of the starting signal until a duty cycle that provides a most significant increase in production of BMP 2 and 4, TGF-beta 1, 2, and 3, FGF-2, osteocalcin, and alkaline phosphatase mRNA is found, and selectively varying an on-off interval of the duty cycle of the signal until an on-off interval that provides a most significant increase in production of BMP 2 and 4, TGF-beta 1, 2, and 3, FGF-2, osteocalcin, and alkaline phosphatase mRNA is found.

19. A method as in claim 18, comprising the further steps of selectively varying a frequency and waveform of said starting signal, keeping other signal characteristics constant, until a most significant increase in production of BMP 2 and 4, TGF-beta 1, 2, and 3, FGF-2, osteocalcin, and alkaline phosphatase mRNA is found.

* * * * *